United States Patent [19]
Ratcliff

[11] Patent Number: 5,834,003
[45] Date of Patent: Nov. 10, 1998

[54] METHOD FOR OXIDATIVELY CONSUMING VOLATILE SULFUR COMPOUNDS AT BODILY ORIFICES

[75] Inventor: Perry A. Ratcliff, Scottsdale, Ariz.

[73] Assignee: Micropure, Inc., Scottsdale, Ariz.

[21] Appl. No.: 831,932

[22] Filed: Apr. 2, 1997

Related U.S. Application Data

[60] Continuation of Ser. No. 444,550, May 19, 1995, Pat. No. 5,618,550, which is a division of Ser. No. 87,606, Jul. 6, 1993, Pat. No. 5,489,435.

[51] Int. Cl.$^6$ .............................. A61K 9/00; A61K 33/00
[52] U.S. Cl. .............................. 424/422; 424/45; 424/49; 424/52; 424/53; 424/57; 424/78.02; 424/427; 424/434; 424/437; 424/430; 424/661; 424/673; 424/676; 424/DIG. 15; 514/944; 514/945; 514/966; 514/967; 514/968
[58] Field of Search .............................. 424/422, 45, 49, 424/52, 53, 57, 78.02, 427, 434, 437, 430, 661, 673, 676, DIG. 15; 514/944, 945, 966, 967, 968

[56] References Cited

U.S. PATENT DOCUMENTS 3,271,242   9/1966   McNicholas ............................ 167/17

OTHER PUBLICATIONS

W. NG and J. Tonzetich, "Effect of Hydrogen Sulfide and Methyl Mercaptan on the Permeability of Oral Mucosa", *J. Dent. Res.*, vol. 6, No. 7, pp. 994–997, Jul. 1984.

I. Kleinberg and G. Westbay, "Salivary and Metabolic Factors Involved in Oral Malodor Formation", pp. 768–774, *J. Periodontol*, vol. 63, No. 9, Sep. 1992.

W.O. Engler, S.P. Ramfjord and J.J. Hiniker, "Development of Epithelial Attachment and Gingival Sulcus in Rhesus Monkeys", *J. Periodontol*, vol. 36, 1965, pp. 44–57.

R.J. Genco, T.E. Van Dyke, M.J. Levine, R.D. Nelson and M.E. Wilson, "Molecular Factors Influencing Defects in Periodontal Disease", 1985 Kreshover Lecture, *J. Dent. Res.*, vol. 65, No. 12, Dec. 1986, pp. 1379–1380.

*Federal Register,* vol. 47, No. 101, Tuesday, May 25, 1982, "Proposed Rules", p. 22801.

J. Tonzetich, "Production and Origin of Oral Malodor: A Review of Mechanisms and Methods of Analysis", *J. Periodontol,* vol. 48, No. 1, Jan. 1977, pp. 13–20.

Anthony A. Rizzo, "The Possible Role of Hydrogen Sulfide in Human Periodontal Disease", *Periodontics,* vol. 5, No. 5, Sep./Oct. 1967, pp. 233, 235, 236.

Maria C. Solis–Gaffar, Thomas J. Fischer and Abdul Gaffar, "Instrumental Evaluation of Odor Produced by Specific Oral Microorganisms", *J. Soc. Cosmet. Chem.,* vol. 30, Jul./Aug. 1979, pp. 241–247.

*Primary Examiner*—Raj Bawa
*Attorney, Agent, or Firm*—Cahill, Sutton & Thomas P.L.C.

[57] ABSTRACT

A method for oxidatively consuming volatile sulfur compounds selected from the group consisting of dimethylsulfide, hydrogen sulfide, and methylmercaptan at the epithelial barrier of the rectal, vaginal, urethral, oral, nasal, ocular, and auditory canal orifices to maintain the epithelial barrier and reduce penetration of any of Candida, *Actinobacillus actinomycetumcomitans*, Pseudomonades, and *Porphyromonas gingivalis,* said method comprising the step of applying to the orifices a composition comprising a topical preparation selected from the group consisting of liquid solutions, suspensions, semi-solids, salves, creams, and suppositories, wherein the topical preparation contains chlorine dioxide in a concentration in the range of about 0.005% to about 2.0% and a phosphate compound selected from the group consisting of disodium hydrogen phosphate, sodium dihydrogen phosphate, trisodiuit phosphate, or sodium monofluorophosphate in a concentration in the range of about 0.02% to about 3.0% to retard escape of chlorine dioxide from the composition at a pH in the range of about 6.0 to about 7.4.

8 Claims, No Drawings

METHOD FOR OXIDATIVELY CONSUMING VOLATILE SULFUR COMPOUNDS AT BODILY ORIFICES

This is a continuation application of Ser. No. 08/444,550, filed May 19, 1995 for "METHOD FOR TREATMENT OF ABNORMAL CONDITIONS OF THE EPITHELIUM OF BODILY ORIFICES", now U.S. Pat. No. 5,618,550, issued Apr. 8, 1997, which is a divisional of application Ser. No. 08/087,606, filed Jul. 6, 1993, now U.S. Pat. No. 5,489,435, issued Feb. 6, 1996.

BACKGROUND OF THE INVENTION

The present invention is directed to a method and composition for prevention and treatment of abnormal conditions of the epithelium of bodily orifices. More particularly, the present invention relates to the use of activated stabilized chlorine dioxide in conjunction with a phosphate compound (to provide stability and as a surfactant or nonsudsing detergent to reduce surface tension on mucosal tissues assisting in the exposure of the epithelial covering to the activated chlorine dioxide), to thereby prevent and treat fungal and bacterial infections of the rectal, vaginal, urethral, oral, nasal, ocular, and auditory canal orifices, and other-abnormal conditions of the epithelium, including leukoplakia.

Thiols, particularly the volatile sulfur compounds such as hydrogen sulfide, methylmercaptan and dimethylsulfide, are recognized in the current literature as being major contributors to the penetration of bacterial toxins through the epithelial barrier into the underlying basal lamina and connective tissue. A. Rizzo, Peridontics, 5: 233–236 (1967); W. Ng and J. Tonzetich, J. Dental Research, 63(7): 994–997 (1984); M. C. Solis-Gaffar, T. J. Fischer and A. Gaffar, J. Soc. Cosmetic Chem., 30: 241–247 (1979); I. Kleinberg and G. Westbay, J. Peridontol, 63(9): 768–774 (1992). The penetration of this barrier makes possible the invasion of antigenic substances such as viral and bacterial toxins and bacteria into the underlying substrate. Thus, by removing the volatile sulfur compounds and maintaining the epithelial barrier there is a reduction in the penetration capacity of antigens and microbiota (A. Rizzo, Peridontics, 5: 233–236 (1967); W. Ng and J. Tonzetich, J. Dental Research, 63(7): 994–997 (1984); M. C. Solis-Gaffar, T. J. Fischer and A. Gaffar, J. Soc. Cosmetic Chem., 30: 241–247 (1979)) as well as the destruction of the motility and the death of bacterial and viral forms.

Studies done in the mouth have demonstrated that the penetration of bacteria takes place in the presence of the volatile sulfur compounds, resulting in initiation of the inflammatory reaction including initiation of the complement cascade. I. Kleinberg and G. Westbay, J. Peridontol, 63(9): 768–774 (1992). Initiation of the inflammatory reaction and development of the complement leads to an eight-fold increase in the cell division or mitosis of epithelial cells in the attachment apparatus of the gingiva. W. O. Engler, S. P. Ramfjiord and J. J. Hiniker, J. Periodont., 36: 44–56 (1965). Because the epithelia of other orifices, and particularly vaginal epithelium, are very similar to the gingival epithelium, reactions similar to those described above for the gingival epithelium, occur in all other parts of the body, as demonstrated by the occurence of vaginitis and endometriosis of the vagina. Examples of such bacteria which may appear in any bodily orifice include *Porphyromonas* (formerly known as *Bacteroides*) *gingivalis, Actinobacillus actinomycetemcomitans,* and Pseudomonades.

The volatile sulfur compounds are generated primarily from the polypeptide chains of the epithelial cell walls, and from the cell walls, pili, fimbrae, and flagella of microorganisms, including fungi, that are part of the normal flora of the organs of the exposed surfaces of the body. The polypeptide chains are composed of a series of amino acids including cysteine, cystine, and methionine, each of which contain sulfur side chains. The death of the microorganisms or the epithelial cells results in degradation of the polypeptide chains into their amino acid components, particularly cysteine and methionine, which then become the source of the sulfur compounds hydrogen sulfide, methylmercaptan and di-methylsulfide which alter the epithelial barrier, permitting penetration of the barrier by antigenic substances.

Penetration of the epitheial barrier by volatile sulfur compounds reduces the capacity of the tissues to protect against bacteria, virus, fungus, and yeast forms. Tonzetich has shown, using $S^{35}$-labelled methylmercaptan, the penetration of thiol through the epithelium, plus the basal lamina, into the underlying connective tissues where it begins degradation of collagen fibers. W. Ng and J. Tonzetich, J. Dental Research, 63(7): 994–997 (1984). In addition, it is the nature of many of the bodily orifices that they are inhabited by both pathogenic and non-pathogenic organisms. If an antibiotic is used to reduce the organisms normally present, opportunistic yeast forms and other pathogenic organisms resistant to the administered antibiotic often invade or multiply at or in the bodily orifices.

Candida species, particularly *Candida albicans*, are the yeasts that primarily affect the mouth and the female vagina. In the mouth, infection by Candida is called Thrush; in the vagina it is called vaginitis.

With the increase of patients having immunocompromising diseases such as AIDS, leukemia, diabetes and immunosuppressing diseases such as stress, alcoholism, etc., a progressively higher percentage of the human population is-susceptible to invasion and growth of bacterial and fungal Candida organisms. In addition, such patients are susceptible to the development of conditions of leukoplakia such as oral hairy leukoplakia and leukoplakia vulvae.

In patients afflicted with diabetes, as well as familial history diabetes, the neutrophil, which is the first line defense cell against foreign antigens, has an altered 110 Dalton surface protein which reduces the capacity of the neutrophil to phagocytizc bacteria by approximately 50%. R. J. Genco, T. E. Van Dyke, M. J. Levine, R. D. Nelson and M. E. Wilson, J. Dental Research, 65(12):1379–1391 (1986). As a result of the development of antibiotics, insulin, and more sophisticated methods of treating diabetes, early deaths of diabetics from infections have been prevented, resulting in a several-fold increase in the number of familial history diabetes in the population. Thus, the increased presence of the diabetes gene in the gene pool of the human race is rapidly increasing, resulting in a higher number of humans with an immunocompromised capacity. This fact in part explains why some women develop vaginitis whenever they are treated with antibiotic drugs.

3. Stability of Chlorine Dioxide

Chlorine dioxide is unstable in agueous solutions at lower pH levels. It is produced commercially and shipped in an aqueous solution in its hydrolytic byproduct forms at 8.3 to 9.0. pH. At that range there is complete retention of the chlorine dioxide hydrolyzed forms within the solution so that a shelf life of from 1–5 years may be achieved. When the pH of chlorine dioxide is lowered to 7.2 or below, chlorine dioxide begins to become activated and, in the gaseous form, it is available for reactivity with thiols, microorganisms, and organic debris in solution.

At present, there is an inadequate capacity of existing pharmaceutical drugs to control Candida infections (IADR symposium, March 1993). The severe diseases may be resistant to the commonly used drugs ketonideozole and nystatin, etc. Other synthetic drugs which are used systemically may have limited effects, and infections are resistant to treatment. Combinations of these drugs systemically and by suppositories may not always work.

In an in vitro study by the present inventor of Candida culture using the protocol of a simulated oral environment as stipulated by the Food and Drug Administration in the *Federal Register*, Vol. 47, No. 101 (May 25, 1982), wherein calf serum is added to the tryptic soy broth inoculated with the Candida, one ml. of the Candida culture was withdrawn and plate counted by standard techniques to determine the baseline content of the Candida population. Both a solution and a slurry of 1 ml. paste containing 0.1% chlorine dioxide with 0.2% phosphate stabilizer plus 2 ml. of distilled water was added to the TSB broth with calf serum. Additional samples were taken at 10, 30 and 60 seconds and again plated to count the remaining Candida. It was found that at 10 seconds there was a 99+% reduction of *Candida albicans* using standard plate count techniques.

In a six month clinical trial by the present inventor, samples were taken from the gingival crevice of the mouth. After treatment of humans with a composition comprising 0.10% chlorine dioxide and 0.2% phosphate stabilizer, the inventor showed by means of standard plate count methods that during the period from baseline to six months, there was a statistically significant reduction of *Candida albicans*. This clinical trial demonstrates the capacity of a composition comprising 0.1% activated stabilized chlorine dioxide together with metallic phosphate (the latter compound acting both to stabilize the chlorine dioxide solution and also as a surfactant to break the surface tension and allow chlorine dioxide to effectively interact with the *Candida albicans* infection) to prevent and treat the development of a Candida infection.

Further details of the preparation and use of chlorine dioxide/phosphate compositions can be found in U.S. Pat. No. 5,200,171, issued Apr. 6, 1993 to Ratcliff, which is hereby incorporated by reference.

SUMMARY OF THE INVENTION

Briefly, and in accord with one embodiment of the present invention, a composition containing stabilized chlorine dioxide and a phosphate is disclosed as being useful in preventing and treating abnormal conditions of the epithelium of bodily orifices. Examples of such abnormal conditions of the epithelium of the rectal, vaginal, urethral, oral, nasal, ocular, and auditory canal orifices include bacterial and fungal infections, such as Candida, and leukoplakia. Stabilized chlorine dioxide is an effective agent for removing thiol compounds for deodorizing the mouth as well as deodorizing other bodily orifices, such as the vagina. The addition of activating inhibitor phosphates to the stabilized chlorine dioxide reduces surface tension and retards the rapid escape of chlorine dioxide gas at the pH range of 6.5 to 7.0 typical of orifices of the body. Preferred concentrations of stabilized chlorine dioxide compounds are in the range of between about 0.005% to 2.0%. The concentration of the phosphate compound, preferably disodium hydrogen phosphate, sodium dihydrogen phosphate, trisodium phosphate, and sodium monofluorophosphate, is in the range of between about 0.02 to 3.0%.

DESCRIPTION OF THE PREFERRED EMBODIMENT

Broadly, the present invention contemplates the use of an activating inhibitor and surface tension reducing agent, specifically, a phosphate compound, preferably, disodium hydrogen phosphate, sodium dihydrogen phosphate, trisodium phosphate, or sodium monofluorophosphate (in particular, trisodium phosphate, or sodium monofluorophosphate), combined with a stabilized chlorine dioxide solution, to make possible the lowering of the pH of the mixture to an optimal value of less than about 7.2 at the time the mixture is used to prevent and treat abnormal conditions of the epithelium of bodily orifices, such as those caused by fungal and bacterial infections of the rectal, vaginal, urethral, oral, nasal, ocular, and auditory canal orifices, and other abnormal conditions of the epithelium, including leukoplakia.

The present invention can be used to control the above-described bodily orifice maladies in humans, and animals which are human companions, such as dogs, cats, horses, etc., by reducing the presence of fungal and bacterial infections and leukoplakia in bodily orifices of the human and animal population, to prevent transference and cross infection from person to person or animal to person or animal to animal. Thus, the present invention can be used in both human and veterinary applications.

Clinical observations and in vitro and in vivo studies by the inventor have led to the discovery that an activating inhibitor phosphate such as disodium monohydrogen phosphate, sodium dihydrogen phosphate, or, preferably, trisodium phosphate, or sodium monofluorophosphate, causes a reduction in surface tension, as well as stabilizing chlorine dioxide, so that the chlorine dioxide remains effective at a lower pH than was previously thought possible. In addition, the phosphate is a detergent which is used in place of other detergents for lowering surface tension and allowing the activated chlorine dioxide to become available to the convoluted surfaces of the body orifices. The preferred concentration ranges are between about 0.005%–2.0% chlorine dioxide, and between about 0.02%–3.0% phosphate. For most patients, the preferred concentration of chlorine dioxide will be in the range of between about 0.005–0.5%; in the case of extremely immunocompromised patients having runaway bacterial or fungal infections or severe leukoplakia, it is preferred to increase the concentration of chlorine dioxide up to about 1.0–2.0%.

The permeability of mucus epithelial tissue is increased substantially by exposure to thiol compounds including hydrogen sulfide ($H_2S$) and methylmercaptan ($CH_3$—$SH$) and dimethylsulfide ($CH_3$—$S$—$CH_3$). In a Candida infection, there is increased inflammation and degeneration of epithelial cells, which break down into thiols, including the above sulfur compounds. A vicious cycle is established, leading to an environment for the increase of Candida growth. If the patient is immunocompromised with AIDS, the problem is exacerbated with ulcerations that could increase the probability of sexually transmitted disease. Likewise, a non-AIDS patient could be more exposed to sexually transmitted disease.

The following examples further illustrate various features of the invention but are intended in no way to limit the scope of the invention which is defined in the appended claims.

EXAMPLE 1

The Stability of Chlorine Dioxide at Ph 6.8 in the Presence of Phosphate.

Materials:

1. Purogene (2% $ClO_2$), Lot #8907.41, 1 gallon, Manufactured by BIO-Cide, International, P.O. Box 2700, Norman, Okla. 73070.

2. Sodium Phosphate, monobasic, dibasic, and tribasic.

Methods:

A 10% solution of monobasic sodium phosphate was prepared in distilled water. Ten ml was placed into each of four beakers. One of each of the four beakers received 1, 2.5, 5, and 10 ml of chlorine dioxide concentrate (2% $ClO_2$), respectively. All solutions were diluted to 90 ml with distilled water, adjusted to pH 6.8 with 1N NaOH and 1N HCl, diluted to 100 ml and placed in screw cap bottles.

Solutions containing dibasic and tribasic sodium phosphate and a distilled water blank control were prepared in a similar manner.

Chlorine dioxide content and pH was determined for each solution on days 0, 7, 14, 21 and 28 in accordance with Standard Methods for the Examination of Water and Wastewater, 17th edition, 1989.

Results and Summary:

As shown in Table 1, the content of chlorine dioxide was stable in all sodium phosphate solutions and distilled water control over the 28 day test period. The pH of all samples ranged from 6.1 to 7.6.

Solutions containing dibasic and tribasic sodium phosphate and a distilled water blank control are prepared in a similar manner.

Chlorine dioxide content and pH is determined for each solution on days 0, 7, 14, 21 and 28 in accordance with Standard Methods for the Examination of Water and Wastewater, 17th edition, 1989, in order to determine the stability of chlorine dioxide over time.

EXAMPLE 3

The Effectiveness of Chlorine Dioxide in Phosphate Mixture Against *Candida albicans*

Materials:

1. Purogene (2% chlorine dioxide), lot #8907:41, manufactured by BIO-CIDE International, Inc., P. 0. Box 2700, Norman, Okla. 73070.
2. Test Organism: *Candida albicans* (ATCC#18804)
3. Saline, 0.9% NaCl.
4. Butterfield's Buffer phosphate dilutent (BFB), pH 7.2.
5. Sterile 15% sodium thiosulfate.
6. Blood agar.
7. Stop watch.

TABLE 1

RESULTS SHOWING THE STABILITY OF CHLORINE DIOXIDE SOLUTION AT pH 6.8 IN DISTILLED WATER AND 1% SODIUM PHOSPHATE, MONOBASIC, DIBASIC AND TRIBASIC

| | Theoretical | DAY | | | | | | | | | |
|---|---|---|---|---|---|---|---|---|---|---|---|
| | | 0 | | 7 | | 14 | | 21 | | 28 | |
| SOLUTION | % $ClO_2$ | pH | % $ClO_2$ | pH | % $ClO_2$ | pH | % $ClO_2$ | pH | % $ClO_2$ | pH | % $ClO_2$ |
| Distilled | 0.02 | 6.8 | 0.02 | 6.9 | 0.02 | 6.9 | 0.02 | 6.5 | 0.02 | 6.5 | 0.02 |
| Water | 0.05 | 6.8 | 0.05 | 6.9 | 0.05 | 6.9 | 0.05 | 7.1 | 0.05 | 6.9 | 0.05 |
| | 0.1 | 6.9 | 0.1 | 6.9 | 0.1 | 7.0 | 0.1 | 7.7 | 0.1 | 7.6 | 0.1 |
| | 0.2 | 6.8 | 0.2 | 6.9 | 0.2 | 6.9 | 0.2 | 7.2 | 0.2 | 7.2 | 0.2 |
| 0/0 $Na_2HPO_{11}$ | 0.02 | 6.8 | 0.02 | 6.1 | 0.02 | 6.7 | 0.02 | 6.7 | 0.02 | 6.8 | 0.02 |
| (Disodium | 0.05 | 6.0 | 0.05 | 6.8 | 0.05 | 6.8 | 0.05 | 6.8 | 0.05 | 6.8 | 0.05 |
| hydrogen | 0.1 | 6.8 | 0.1 | 6.9 | 0.1 | 6.9 | 0.1 | 6.8 | 0.1 | 6.8 | 0.1 |
| phosphate) | 0.2 | 6.8 | 0.2 | 6.9 | 0.2 | 6.9 | 0.2 | 6.9 | 0.2 | 6.8 | 0.2 |
| 0/0 $NaH_2PO_4$ | 0.02 | 6.8 | 0.02 | 6.7 | 0.02 | 6.8 | 0.02 | 6.7 | 0.02 | 6.8 | 0.02 |
| (Sodium | 0.05 | 6.8 | 0.05 | 6.8 | 0.05 | 6.8 | 0.05 | 6.8 | 0.05 | 6.9 | 0.05 |
| dihydrogen | 0.1 | 6.8 | 0.1 | 6.8 | 0.1 | 6.8 | 0.1 | 6.9 | 0.1 | 6.9 | 0.1 |
| phosphate) | 0.2 | 6.8 | 0.2 | 6.8 | 0.2 | 6.8 | 0.2 | 6.9 | 0.2 | 6.9 | 0.2 |
| 0/0 $Na_3PO_4$ | 0.02 | 6.8 | 0.02 | 6.8 | 0.02 | 6.4 | 0.02 | 6.9 | 0.02 | 7.0 | 0.02 |
| (Trisodium | 0.05 | 6.8 | 0.05 | 7.0 | 0.05 | 7.1 | 0.05 | 6.9 | 0.05 | 7.0 | 0.05 |
| phosphate) | 0.1 | 6.8 | 0.1 | 7.5 | 0.1 | 7.5 | 0.1 | 7.0 | 0.1 | 6.9 | 0.1 |
| | 0.2 | 6.8 | 0.2 | 7.0 | 0.2 | 7.1 | 0.2 | 6.9 | 0.2 | 6.9 | 0.2 |

EXAMPLE 2

The Stability of Chlorine Dioxide at Ph 6.8 in the Presence of 0.2% Phosphate

The following is an example of how to test the stability of chlorine dioxide at pH 6.8 in the presence of 0.2% phosphate.

Materials:

1. Purogene (2% $ClO_2$), Lot #8907.41, 1 gallon, Manufactured by BIO-Cide, International, P.O. Box 2700, Norman, Okla. 73070.
2. Sodium Phosphate, monobasic, dibasic, and tribasic.

Methods:

A 0.2% solution of monobasic sodium phosphate is prepared in distilled water. Ten ml is placed into each of four beakers. One of each of the four beakers receives 1, 2.5, 5, and 10 ml of chlorine dioxide concentrate (2% $ClO_2$), respectively. All solutions were diluted to 90 ml with distilled water, adjusted to pH 6.8 with 1N NaOH and 1N HCl, diluted to 100 ml and placed in screw cap bottles.

8. Sterile 1N HCl and 1N NaOH.
9. pH meter.
10. McFarland nephelometer tube No. 1. Density of this tube is equivalent to a bacterial suspension of $3 \times 10^8$ organisms per ml.
11. N,N-diethyl-p-phenylenediamine (DPD reagent).
12. Phosphate buffer reagent.
13. Sodium dihydrogen phosphate, $NaH\ PO_4 \cdot 7H_2O$.
14. Trisodium phosphate, $Na_3PO_4 \cdot 12H_2O$.
15. Sodium monofluorophosphate, $Na_2FPO_3$, Ref No. OB 12837, manufactured by Albright and Wilson, P.O. Box 80, Oldbury, Narley, West Midlands, B694LN, England.

DPD reagent and phosphate buffer reagent were prepared in accord with Standard Methods for the Examination of Water and Wastewater, 17th Edition, p. 9–54 (1989).

Methods:

1. Test Solutions:

A ten percent sodium dihydrogen phosphate solution was prepared in distilled water. Ten ml was placed into each of five beakers. One of each of the five beakers received 0, 1, 2.5, 5, and 10ml of chlorine dioxide concentrate (2% $ClO_2$), respectively. All solutions were diluted to 90 ml with distilled water, adjusted to pH 6.0 with 1N NaOH and 1N HCl, diluted to 100 ml and placed in screw cap bottles. Solutions containing 0 ppm chlorine dioxide were filter sterilized prior to use.

Solutions containing trisodium phosphate and sodium monofluorophosphate were prepared in a similar manner.

II. Test Suspensions:

Suspensions of the *Candida albicans* organism were prepared in Butterfield's buffer from 48 hour agar cultures and turbidity adjusted to a McFarland Tube #1. Subsequently 0.1 ml of this suspension was diluted in 50 ml of saline. The diluted microorganism suspensions were now ready for use.

III. Test Procedure:

1. Test:

One ml of test suspension was aliquoted into each of five sterile 16×125 mm screw cap tubes. Each of the five tubes received 4 ml of a solution containing either 0, 200, 500, 1000, or 2000 ppm chlorine dioxide in 1% sodium dihydrogen phosphate. Each tube was shaken for ten seconds and immediately inactivated with 0.25 ml 15% sodium thiosulfate. Solutions containing 1% trisodium phosphate and 1% sodium monofluorophosphate were handled in a similar manner.

2. Controls:

One ml of test suspension was dispensed into two sterile 16×125 mm screw cap tubes. Each tube received 4 ml 2000 ppm chlorine dioxide in 1% sodium dihydrogen phosphate. The first tube received 0.25 ml sodium thiosulfate, while the second tube received none. Subsequently each tube was tested for residual chlorine dioxide by adding 0.3 ml phosphate buffer reagent and 0.3 ml DPD reagent to each tube. Neutralized tubes were colorless, while nonneutralized tubes were pink. Solutions of trisodium phosphate and sodium monofluorophosphate containing 2,000 ppm chlorine dioxide were handled in a similar manner.

One ml test suspension of the *Candida albacans* organism was treated with 4 ml Butterfield's buffer and 0.25 ml 10% sodium thiosulfate as a negative control.

After inactivation with sodium thiosulfate all tubes were plate counted.

Sterility tests on all reagents were run parallel to experiments by plate counted method. The plate counted method and sterility tests were conducted in accord with Standard Methods for the Examination of Water and Wastewater, 17th Edition, p. 9–54 (1989).

Results and Summary:

As shown in Table 2, 99–100% of the *Candida albicans* organisms were killed when challenged with 1,000 ppm (0.1%)–2,000 ppm (0.2%) chlorine dioxide in either 1% sodium dihydrogen phosphate or trisodium phosphate. Chlorine dioxide concentrations of 200 (0.02%) and 500 ppm (0.05%) in the presence of phosphates demonstrated marginal bacteriocidal activity against *C. albicans* (39–51% kill).

TABLE 2

RESULTS SHOWING THE BACTERIOCIDAL ACTIVITY OF CHLORINE DIOXIDE IN PHOSPHATE SOLUTIONS AT pH 6.0 AGAINST *CANDIDA ALBICANS*

| | | PHOSPHATE SOLUTION | |
|---|---|---|---|
| $ClO_2$ (PPM) | Negative Control[x] | 1% $NaH_2PO_4$ | 1% $Na_2PO_4$ |
| 0 | 95,000[xx] | 64,000 (33)[xxx] | 55,000 (42) |
| 200 | ND | 58,000 (39) | 64,000 (33) |
| 500 | ND | 47,000 (51) | 32,000 (66) |
| 1000 | ND | 250 (99) | 0 (100) |
| 2000 | ND | 17 (99) | 5 (99) |

[x]Butterfield's buffer
[xx]Organisms/ml
[xxx]Percent Kill
ND = Not Done

EXAMPLE 4

The Effectiveness of Chlorine Dioxide in Phosphate Mixture Against *Candida Albicans* in The Presence and Absence of Serum Materials:

1. Purogene, Lot #8907:41, 1 gallon (contains 2% $ClO_2$), manufactured by BIO-CIDE International, Inc., P.O. Box 2700, Norman, Okla. 73070.
2. Test Organism: *Candida albicans* (ATCC #18804) obtained from American Type Culture Collection, (ATCC) 12301 Parklawn Drive, Rockville, Md. 20852.
3. 15% Sodium thiosulfate ($Na_2S_2O_3$)
4. Plate Count agar
5. Newborn calf serum, Colostrum free, Lot #30P7485, Gibco Laboratories, Grand Island, N.Y. 14072.
6. Butterfield's Buffer, pH 7.2
7. Trisodium phosphate, $Na_3PO_4 \cdot 12H_2O$, Sigma Chemical Co., St. Louis, Mo. 63178.

Methods:

Chlorine dioxide solution having concentrations of 0, 200, 500, 1,000 and 2,000 mg/L were prepared from Purogene concentrate. Each $ClO_2$ concentration was prepared to contain 0.5% tribasic sodium phosphate (i.e., trisodium phosphate, $Na_3PO_4 \cdot 12H_2O$). In a similar manner, chlorine dioxide solutions of 0, 200, 500, 1,000 and 2,000 mg/L were prepared, with each solution containing 1.0% tribasic sodium phosphate. The pH of the chlorine dioxide/phosphate mixture was adjusted to 6.5 with 1N and 6N hydrochloric acid.

Tryptic Soy Broth (100 ml) was innoculated with *Candida albicans* and incubated 24 hours at 35° C. After incubation, the cells were washed three times with Butterfield's buffer and resuspended in 100 ml buffer.

Testing in the Absence of Serum:

Chlorine dioxide-phosphate solutions (100 ml) were dispensed into sterile 16×125 mm screw cap tubes, 9 ml/tube. Three tubes were prepared for each $ClO_2$ concentration. One ml of washed *C. albicans* suspension was added to one tube of each $ClO_2$ concentration, and mixed vigorously for 10 seconds. One minute after addition of $ClO_2$, 2 ml of 15% sodium thiosulfate ($Na_2S_2O_3$) was added to each tube and well mixed to inactivate the mixture. The procedure was repeated twice with the remaining tubes except that $ClO_2$ was inactivated with sodium thiosulfate after 2 and 5 minutes respectively.

Serial ten-fold dilutions ($10^{-1}$–$10^{-5}$) of *Candida albicans*/$ClO_2$ mixtures were prepared in Butterfield's buffer. Simultaneously, one ml of each dilution was transferred to a sterile 15 mm petri dish. Then 10 ml of plate count agar at 45°–47° C. was added to each plate, and the plates were swirled and allowed to solidify. Plates were inverted and incubated 76 hours at 35° C., and colonies counted.

Testing in Presence of Serum:

Chlorine dioxide-phosphate solutions, were aliquoted, 8 ml/tube. Three tubes were prepared per $ClO_2$ concentration. Fifty ml washed *C. albicans* suspension was added with 50 ml newborn calf serum. 2 ml of the serum-*C. albicans* suspension was added to test tubes and processed as described above.

Results:

Results showing percent kill of *Candida albicans* as a result of application of chlorine dioxide-phosphate solutions are shown in Tables 3 and 4.

TABLE 3

Results Showing Bacteriocidal Activity of Chlorine Dioxide-Phosphate (0.5%) Solutions at pH 6.5 Against *Candida Albicans*

| Time | $ClO_2$ w/out Serum (ppm) | | | | $ClO_2$ w/Serum (ppm) | | | |
| --- | --- | --- | --- | --- | --- | --- | --- | --- |
| (Seconds) | 200 | 500 | 1000 | 2000 | 200 | 500 | 1000 | 2000 |
| 1 | 33* | 44 | 99+ | 99+ | <10 | 27 | 18 | 36 |
| 2 | 13 | 33 | 99+ | 99+ | 40 | 30 | 30 | 30 |
| 5 | 29 | 35 | 99+ | 99+ | 13 | <10 | <10 | ND |

*Percent kill
ND = Not done
+ = greater than

TABLE 4

Results Showing Bacteriocidal Activity of Chlorine Dioxide-Phosphate (1%) Solutions at pH 6.5 Against *Candida Albicans*

| Time | $ClO_2$ w/out Serum (ppm) | | | | $ClO_2$ w/Serum (ppm) | | | |
| --- | --- | --- | --- | --- | --- | --- | --- | --- |
| (Seconds) | 200 | 500 | 1000 | 2000 | 200 | 500 | 1000 | 2000 |
| 1 | 30* | 65 | 99+ | 99+ | <10 | <10 | <10 | <10 |
| 2 | 37 | 47 | 99+ | 99+ | 19 | <10 | 29 | 19 |
| 5 | 17 | ND | 99+ | 99+ | <10 | <10 | <10 | <10 |

*Percent kill
ND = Not done
+ = greater than

EXAMPLE 5

The Effectiveness of Chlorine Dioxide in Phosphate Mixture Against *Actinobacillus actinomycetemcomitans* in the Presence and Absence of Serum Materials:

1. Purogene; Lot 98907:41, 1 gallon (contains 2% ClO.), manufactured by BIO-CIDE International, Inc., P.O. Box 2700, Norman, Okla. 73070.
2. *Actinobacillus actinomycetemcomitans*, ATCC #29522, obtained from American Type Culture Collection, 12301, Parklawn Drive, Rockville, Md. 20852.
3. 15% Sodium thiosulfate ($Na_2S_2O_3$)
4. Plate Count agar
5. Newborn calf serum, Colostrum free, Lot #30P7485, Gibco Laboratories, Grand Island, N.Y., 14072.
6. Butterfield's Buffer, pH 7.2
7. Trisodium phosphate, $Na_3PO_4.12H_2O$, Sigma Chemical Co., St. Louis, Mo. 63178

Methods:

Chlorine dioxide solutions having concentrations of 1,000 and 2,000 mg/L were prepared from Purogene concentrate. Each $Cl_2$ concentration was prepared to contain 0.2% sodium phosphate, tribasic (i.e., trisodium phosphate, $Na_3PO_4.12H_2O$). The pH of the chlorine dioxide/phosphate mixture was adjusted to 6.5 with 1N hydrochloric acid.

Three chocolate agar plates were inoculated with *Actinobacillus actinomycetemcomitans* and incubated 48 hours at 35° C. in a candle jar. After incubation, cells were scraped from the plates with a cotton swab and suspended in 100 ml buffer. 50 ml of this suspension was diluted with 50 ml buffer, while the other 50 ml was diluted with 50 ml serum.

Testing in the Absence of Serum:

Chlorine dioxide-phosphate solutions (100 ml) were dispensed into sterile 150 ml beakers containing magnetic stir bars. While stirring on a magnetic mixer, a 10 ml portion of *A. actinomycetemcomitans*-buffer suspension was added. At 10, 30 and 60 second intervals, 10 ml was removed from the beaker and transferred to a 16×125 mm tube which contained 2 ml 15% sodium thiosulfate. The tube was capped, mixed, and a plate count was performed employing chocolate agar as the growth media, in accord with the methods described in *FDA Bacteriological Analytical Manual*, 6th edition, 1984, chapters 4, 17, herein incorporated by reference.

Testing in Presence of Serum:

Testing in the presence of serum was handled in a similar manner, except that an *Actinobacillus actinomycetemcomitans*-serum suspension was substituted for the *Actinobacillus actinomycetemcomitans*-buffer suspension.

Results:

Results showing percent kill of *Actinobacillus actinomycetemcomitans* following application of the chlorine dioxide-phosphate solutions are shown in Table 5.

TABLE 5

Results Showing Bacteriocidal Activity of Chlorine Dioxide-Phosphate (0.2%) at pH 6.5 Against *Actinobacillus Actinomycetemcomitans*

| TIME | $ClO_2$ w/out Serum (ppm) | | $ClO_2$ w/ Serum (ppm) | |
| --- | --- | --- | --- | --- |
| (Seconds) | 1000 | 2000 | 1000 | 2000 |
| 10 | 99* | 99+ | 99+ | 99+ |
| 30 | 99+ | 99+ | 99+ | 99+ |
| 60 | 99+ | 99+ | 99+ | 99+ |

*Percent kill
+ = greater than

EXAMPLE 6

The Effectiveness of Chlorine Dioxide in Phosphate Mixture Against *Porphyromonas Gingivalis* in the Presence and Absence of Serum Materials:

1. Purogene, Lot #8907:41, 1 gallon (contains 2% $ClO_2$) manufactured by BIO-CIDE International, Inc., P.O. Box 2700, Norman, Okla. 73070.
2. *Porohyromonas* (formerly known as *Bacteroides*) *gingivalis*, ATCC # 33277, obtained from American Type Culture Collection, 12301 Parklawn Drive, Rockville, Md. 20852.

3. 15% Sodium thiosulfate ($Na_2S_2O_3$)
4. Plate Count agar
5. Newborn calf serum, Colostrum free, lot #30P7485, Gibco Laboratories, Grand Island, N.Y., 14072.
6. Butterfield's Buffer, pH 7.2
7. Trisodium phosphate, $Na_3PO_4 \cdot 12H_2O$, Sigma Chemical Co., St. Louis, Mo. 63178.

Methods:

Chlorine dioxide solutions having concentrations of 1,000 and 2,000 mg/L were prepared from Purogene concentrate. Each $ClO_2$ concentration was prepared to contain 0.2% sodium phosphate, tribasic (i.e., trisodium phosphate, $Na_3PO_4 \cdot 12H_2O$). The pH of the chlorine dioxide/phosphate mixture was adjusted to 6.5 with 1N hydrochloric acid. Three anaerobic BAP plates were inoculated with *gingivalis* (ATCC 33277) and incubated 72 hours at 35° C. After incubation, cells were scraped from the plates with a cotton swab and suspended in 100 ml buffer. 50 ml of this suspension was diluted with 50 ml buffer, while the other 50 ml was diluted with 50 ml serum.

Testing in the Absence of Serum:

Chlorine dioxide-phosphate solutions (100 ml) were dispensed into sterile 150 ml beakers containing magnetic stir bars. While stirring on a magnetic mixer, a 10 ml portion of *P. gingivalis*-buffer suspension was added. At 10, 30 and 60 second intervals, 10 ml was removed from the beaker and transferred to a 16×125 mm tube which contained 2 ml 15% sodium thiosulfate. Tube was capped, mixed, and an anaerobic plate count was performed using anaerobic blood agar in accord with the methods described in *FDA Bacteriological Analytical Manual*, 6th edition, 1984, chapter 17.

Testing in Presence of Serum:

Testing in the presence of serum was handled in a similar manner to that described immediately above, except that a *Porphyromonas gingivalis*-serum suspension was substituted for the *Porphyromonas gingivalis*-buffer suspension.

Results:

Results showing percent kill of *Porphyromonas gingivalis* by application of chlorine dioxide-phosphate solutions are shown in Table 6.

TABLE 6

Results Showing Bacteriocidal Activity of Chlorine Dioxide-Phosphate (0.2%) Solutions at pH 6.5 Against *Porphyromonas Gingivalis*

| TIME | $ClO_2$ w/out Serum (ppm) | | $ClO_2$ w/ Serum (ppm) | |
| --- | --- | --- | --- | --- |
| (Seconds) | 1000 | 2000 | 1000 | 2000 |
| 10 | 89* | 99+ | 82 | 86 |
| 20 | 99+ | 99+ | 84 | 97 |
| 60 | 99+ | 99+ | 94 | 99 |

*Percent kill
+ = greater than

EXAMPLE 7

A boy diagnosed as having Thrush was treated with the drug ketonideozole for two weeks. The Candida were not controlled. The boy was then treated with a mouthrinse solution and toothpaste both of which contained as the effective ingredient a composition comprising 0.1% chlorine dioxide together with 0.2% trisodium phosphate. The boy's Thrush infection was brought under control within 3 days. The treating pediatrician was surprised and did not understand how the boy's recovery could happen so quickly.

EXAMPLE 8

The present inventor has treated hairy leukoplakia present on the tongue of AIDS-infected patients. The daily use of a toothpaste and mouthrinse, both of which contained as the effective ingredient a composition comprising 0.1% chlorine dioxide together with 0.2% trisodium phosphate, resulted in the disappearance of the hairy leukoplakia within 14 days. When the chlorine dioxide/phosphate-containing products were withdrawn, the hairy leukoplakia returned within 14 days. When the same products were again administered, the hairy leukoplakia again disappeared.

EXAMPLE 9

Hypothetically, the following composition may be prepared:

| Stabilized chlorine dioxide | at least 0.1% |
| --- | --- |
| Phosphate compound | at least 0.05% |

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the vagina of a patient afflicted with vaginitis. It is predicted that the patient will experience a cessation of vaginitis symptoms as a result of the regular administration of the composition.

EXAMPLE 10

Hypothetically, the following composition may be prepared:

| Stabilized chlorine dioxide | at least 0.1% |
| --- | --- |
| Phosphate compound | at least 0.05% |

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the vagina of a patient afflicted with leukoplakia vulvae. It is predicted that the patient will experience a cessation of the leukoplakia vulvae symptoms as a result of the regular administration of the composition.

EXAMPLE 11

Hypothetically, the following composition may be prepared:

| Stabilized chlorine dioxide | at least 0.1% |
| --- | --- |
| Phosphate compound | at least 0.05% |

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the urethra of a patient infected in that orifice with *Actino-*

*bacillus actinomycetemcomitans*. It is predicted that the patient will experience a cessation of symptoms of the infection as a result of the regular administration of the composition.

EXAMPLE 12

Hypothetically, the following composition may be prepared:

| Stabilized chlorine dioxide | at least 0.1% |
|---|---|
| Phosphate compound | at least 0.05% |

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the vagina of a patient infected in that orifice with *Porphyromonas gingivalis*. It is predicted that the patient will experience a cessation of symptoms of the infection as a result of the regular administration of the composition.

EXAMPLE 13

Hypothetically, the following composition may be prepared:

| Stabilized chlorine dioxide | at least 0.1% |
|---|---|
| Phosphate compound | at least 0.05% |

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the rectum of a patient infected in that orifice with *Porphyromonas gingivalis*. It is predicted that the patient will experience a cessation of symptoms of the infection as a result of the regular administration of the composition.

EXAMPLE 14

Hypothetically, the following composition may be prepared:

| Stabilized chlorine dioxide | at least 0.1% |
|---|---|
| Phosphate compound | at least 0.05% |

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the auditory canal of a patient infected in that orifice with *Actinobacillus actinomycetemcomitans*. It is predicted that the patient will experience a cessation of symptoms of the infection as a result of the regular administration of the composition.

EXAMPLE 15

Hypothetically, the following composition may be prepared:

| Stabilized chlorine dioxide | at least 0.1% |
|---|---|
| Phosphate compound | at least 0.05% |

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the nasal canal of a patient infected in that orifice with *Porphyromonas gingivalis*. It is predicted that the patient will experience a cessation of symptoms of the infection as a result of the regular administration of the composition.

EXAMPLE 16

Hypothetically, the following composition may be prepared:

| Stabilized chlorine dioxide | at least 0.1% |
|---|---|
| Phosphate compound | at least 0.05% |

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the ocular canal of a patient infected in that orifice with *Actinobacillus actinomycetemcomitans*. It is predicted that the patient will experience a cessation of symptoms of the infection as a result of the regular administration of the composition.

EXAMPLE 17

Hypothetically, the following composition may be prepared:

| Stabilized chlorine dioxide | 1.0–2.0% |
|---|---|
| Phosphate compound | at least 0.05% |

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the bodily orifices of a severely immunocompromised patient afflicted with leukoplakia, and with opportunistic bacterial and fungal infections. It is predicted that the patient will experience a cessation of leukoplakia and symptoms of infection as a result of the regular administration of the composition.

EXAMPLE 18

A secretary in the employ of the present inventor developed a vaginitis. She called for an appointment with her gynecologist only to learn that she could not be seen for several days. Because of the extreme itching, and knowing, as a consequence of her employment with the present inventor, that activated chlorine dioxide would kill Candida, she of her own initiation and volition used as a douche a mouthrinse developed by the present inventor, which mouthrinse contains 0.1% activated chlorine dioxide and 0.2% trisodium phosphate. She reported that she was asymptomatic immediately upon application of the above composition, with no itching. She took a wet cloth and applied the above composition locally, in the vicinity of the vagina, for three or four days, with no recurrent symptoms.

In the practice of methods to use the compounds of the present invention, an effective amount of the chlorine dioxide/phosphate composition is administered to the subject in need of, or desiring, such treatment. These compounds or compositions may be administered by any of a variety of routes depending upon the specific end use, including topically, as a lotion, creme or solution, by lavage, suppository, or as a nasal drop or spray.

The most suitable route in any given case will depend upon the use, particular active ingredient, the subject involved, and the judgment of the medical practitioner.

A further aspect of the present invention relates to pharmaceutical compositions containing as active ingredients a compound of the present invention which compositions comprise such compound in admixture with a pharmaceutically acceptable, nontoxic carrier. As mentioned above, such compositions may be prepared for use for topical application, particularly in the form of liquid solutions, suspensions, semi-solids, salves or creams, suppositories, or intranasally particularly in the form of nasal drops or aerosols.

It will be readily apparent to those skilled in the art that a number of modifications and changes can be made without departing from the spirit and scope of the present invention. Therefore, it is not intended that the invention be limited by the illustrative examples but only by the claims which follow.

I claim:

1. A method for oxidatively consuming volatile sulfur compounds selected from the group consisting of dimethylsulfide, hydrogen sulfide, and methylmercaptan at the epithelial barrier of the vaginal orifice to maintain the epithelial barrier and reduce penetration of any of Candida, *Actinobacillus actinomycetumcomitans*, Pseudomonades, and *Porphyromonas gingivalis*, said method comprising the step of applying to the vaginal orifice a composition comprising a topical preparation selected from the group consisting of liquid solutions, suspensions, semi-solids, salves, creams, and suppositories, wherein the topical preparation contains chlorine dioxide in a concentration in the range of about 0.005% to about 2.0% and a phosphate compound selected from the group consisting of disodium hydrogen phosphate, sodium dihydrogen phosphate, trisodium phosphate, or sodium monofluorophosphate in a concentration in the range of about 0.02% to about 3.0% to retard escape of chlorine dioxide from the composition at a pH in the range of about 6.0 to about 7.4.

2. A method for oxidatively consuming volatile sulfur compounds selected from the group consisting of dimethylsulfide, hydrogen sulfide, and methylmercaptan at the epithelial barrier of the vaginal orifice to maintain the epithelial barrier and reduce penetration of any of Candida, *Actinobacillus actinomycetumcomitans*, Pseudomonades, and *Porphyromonas gingivalis*, said method comprising the step of applying to the vaginal orifice a composition comprising a topical preparation selected from the group consisting of liquid solutions, suspensions, semi-solids, salves, creams, and suppositories, wherein the topical preparation contains chlorine dioxide in a concentration of at least 0.1% and a phosphate compound selected from the group consisting of disodium hydrogen phosphate, sodium dihydrogen phosphate, trisodium phosphate, or sodium monofluorophosphate in a concentration of at least 0.05% to retard escape of chlorine dioxide from the composition at a pH in the range of about 6.0 to about 7.4.

3. A method for oxidatively consuming volatile sulfur compounds selected from the group consisting of dimethylsulfide, hydrogen sulfide, and methylmercaptan at the epithelial barrier of the rectal, vaginal, urethral, oral, nasal, ocular, and auditory canal orifices to maintain the epithelial barrier and reduce penetration of any of Candida, *Actinobacillus actinomycetumcomitans*, Pseudomonades, and *Porphyromonas gingivalis*, said method comprising the step of applying to the orifices a composition comprising a topical preparation selected from the group consisting of liquid solutions, suspensions, semi-solids, salves, creams, and suppositories, wherein the topical preparation contains chlorine dioxide in a concentration in the range of about 0.005% to about 2.0% and a phosphate compound selected from the group consisting of disodium hydrogen phosphate, sodium dihydrogen phosphate, trisodium phosphate, or sodium monofluorophosphate in a concentration in the range of about 0.02% to about 3.0% to retard escape of chlorine dioxide from the composition at a pH in the range of about 6.0 to about 7.4.

4. A method for oxidatively consuming volatile sulfur compounds selected from the group consisting of dimethylsulfide, hydrogen sulfide, and methylmercaptan at the epithelial barrier of the rectal, vaginal, urethral, oral, nasal, ocular, and auditory canal orifices to maintain the epithelial barrier and reduce penetration of any of Candida, *Actinobacillus actinomycetumcomitans*, Pseudomonades, and *Porphyromonas gingivalis*, said method comprising the step of applying to the orifices a composition comprising a topical preparation selected from the group consisting of liquid solutions, suspensions, semi-solids, salves, creams, and suppositories, wherein the topical preparation contains chlorine dioxide in a concentration of at least 0.1% and a phosphate compound selected from the group consisting of disodium hydrogen phosphate, sodium dihydrogen phosphate, trisodium phosphate, or sodium monofluorophosphate in a concentration of at least 0.05% to retard escape of chlorine dioxide from the composition at a pH in the range of about 6.0 to about 7.4.

5. The method as set forth in claim 1 wherein the epithelium of the vaginal orifice includes a condition of leukoplakia.

6. The method as set forth in claim 2 wherein the epithelium of the vaginal orifice includes a condition of leukoplakia.

7. The method as set forth in claim 3 wherein the orifice includes a condition of leukoplakia.

8. The method as set forth in claim 4 wherein the orifice includes a condition of leukoplakia.

* * * * *